(12) United States Patent
Gibertoni et al.

(10) Patent No.: US 6,219,490 B1
(45) Date of Patent: Apr. 17, 2001

(54) VENTILATION TUBE, PARTICULARLY FOR MEDICAL DEVICES

(75) Inventors: Lucio Gibertoni, Mirandola; Paolo Bergamaschi, Concordia, both of (IT)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/202,332

(22) PCT Filed: Jun. 10, 1997

(86) PCT No.: PCT/US97/09770

§ 371 Date: May 10, 1999

§ 102(e) Date: May 10, 1999

(87) PCT Pub. No.: WO97/47348

PCT Pub. Date: Dec. 18, 1997

(30) Foreign Application Priority Data

Jun. 13, 1996 (IT) .................................. MI96U0435

(51) Int. Cl.⁷ ........................................................ H05B 3/40
(52) U.S. Cl. .......................... 392/472; 392/480; 392/472; 138/33

(58) Field of Search ........................... 392/478, 472, 392/480, 481; 138/33, 118, 181.1, 121

(56) References Cited

U.S. PATENT DOCUMENTS

| | | | |
|---|---|---|---|
| 3,891,007 * | 6/1975 | Kleykamp | 138/121 |
| 3,963,856 * | 6/1976 | Carlson et al. | 174/47 |
| 4,038,519 * | 7/1977 | Foucras | 219/301 |
| 4,688,603 * | 8/1987 | Donnerhack et al. | 138/103 |
| 5,454,061 * | 9/1995 | Carlson | 392/478 |

* cited by examiner

*Primary Examiner*—Teresa Walberg
*Assistant Examiner*—Shawntina Fuqua
(74) *Attorney, Agent, or Firm*—Lawrence L. Limpus

(57) ABSTRACT

The present invention relates to a ventilation tube particularly for medical devices, which has the particularity that it comprises a tubular body made of flexible plastics which forms raised ridges on its outer surface. An electric wire is embedded in at least part of the ridges and forms an electric resistor for heating the gaseous substance that flows inside the tubular body.

13 Claims, 1 Drawing Sheet

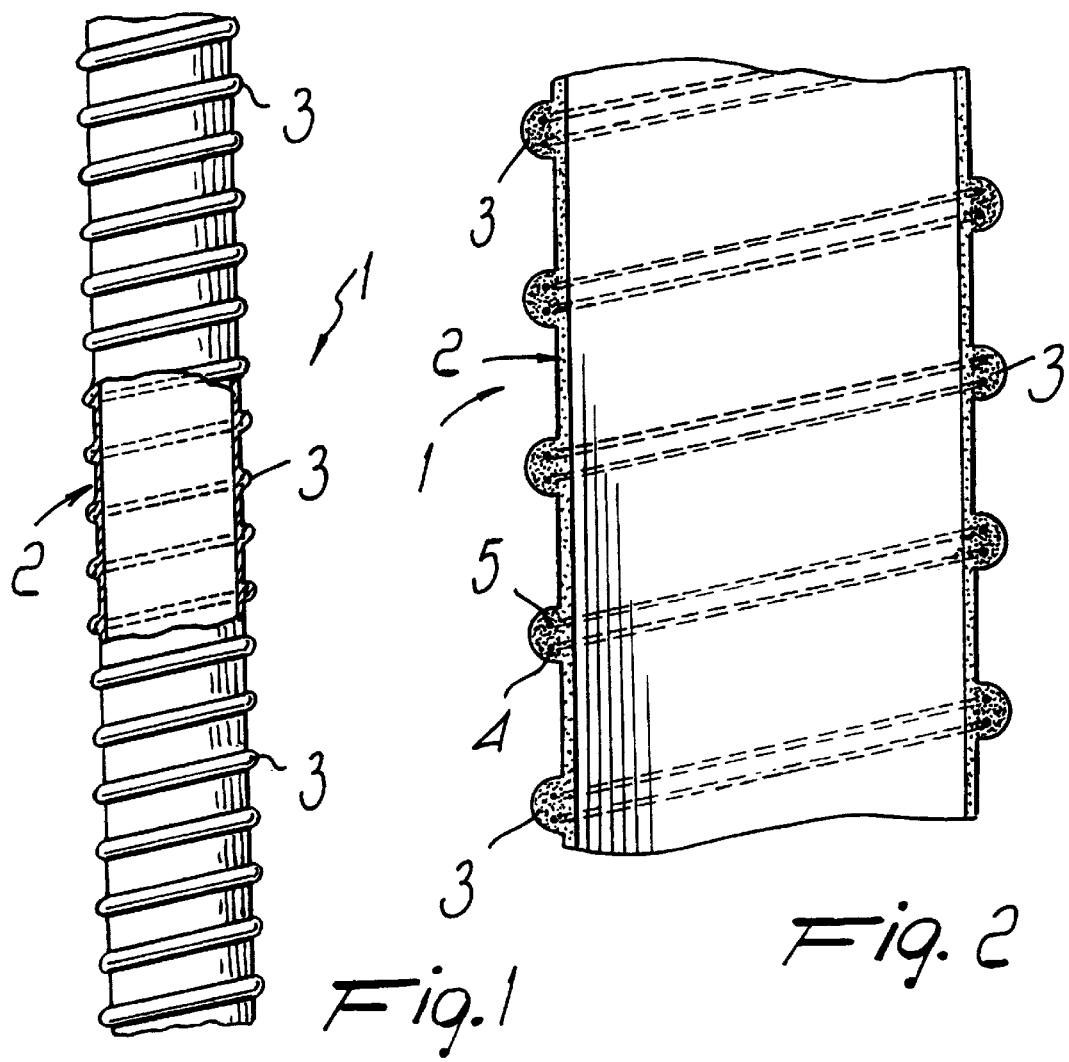
Fig. 1
Fig. 2
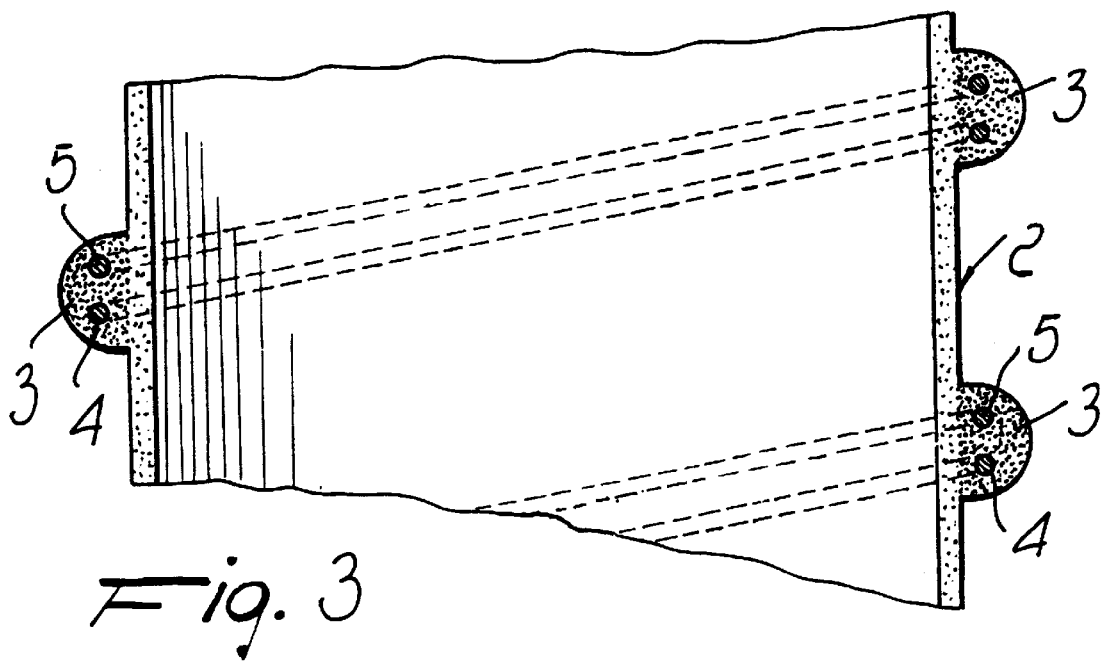
Fig. 3

VENTILATION TUBE, PARTICULARLY FOR MEDICAL DEVICES

TECHNICAL FIELD

The present invention relates to a ventilation tube particularly for medical devices.

BACKGROUND ART

In many medical devices and particularly in ventilation tubes for intensive care, in ventilation tubes at the outlet of humidifiers and the like, it is conventionally necessary to heat the gaseous substance, generally air, that circulates inside the tube.

An electric resistor is currently used to solve the problem, said resistor being located inside the plastic tube, so as to heat the air to prevent condensation of the moisture contained therein.

This solution entails considerable drawbacks, since any burns caused by the electric resistor on the tube wall might generate fumes which would be fed to the patient, with the obvious associated problems.

Another drawback is also constituted by the fact that a resistor located. inside the tube is unable to provide for uniform heating of the inside walls of the tube and therefore cold spots may form which constitute condensation regions for the moisture that is present in ventilation cases, accordingly creating regions in which water accumulates and which, in addition to obstructing the useful cross-section of the tube, also constitute regions for bacterial growth.

In order to solve the above problem, ventilation tubes are already commercially available in which an external wire is provided which is wound in a spiral around the outer wall of the tube; this solution is considerably expensive and also causes problems, since it is necessary to provide for an additional tube in order to sheath the resistor, both owing to electrical insulation problems and in order to prevent excessively hot spots from remaining on the outside, possibly leading to problems for users.

This structure has the drawback that it is very heavy and that it considerably reduces the transparency, lightness and flexibility characteristics which are typical of a PVC tube.

Another drawback resides in the costs, since the sheathing of the tube, in addition to increasing the amount of plastics being used, requires much more complex and expensive production technologies than the ordinary spiral tube.

DISCLOSURE OF THE INVENTION

The aim of the present invention is to solve the above problems, by providing a ventilation tube particularly for medical devices which allows to provide uniform heating on the entire surface of the tube affected by the flow of the gaseous substance, thus helping to eliminate the regions where liquid might condense.

Within the scope of this aim, a particular object of the invention is to provide a ventilation tube in which the heating element is not located inside the tube, so that any burns do not produce fumes which are fed directly to the patient, and is furthermore capable of maintaining the flexibility, lightness and transparency characteristics of the spiral tube substantially unchanged.

Another object of the present invention is to provide a ventilation tube which allows to obtain tubes which are already equipped with the heating element, with the possibility of performing extremely simple connections.

Another object of the present invention is to provide a ventilation tube particularly for medical devices, which can be easily obtained starting from commonly commercially available elements and materials and which is also competitive from a merely economical point of view.

BRIEF DESCRIPTION OF THE DRAWINGS

This aim, these objects, and others which will become apparent hereinafter are achieved by a ventilation tube particularly for medical devices, illustrated only by way of non-limitative example in the accompanying drawings, wherein:

FIG. 1 is a partially cutout schematic view of a portion of ventilation tube according to the present invention;

FIG. 2 is a enlarged-scale sectional view of the tube;

FIG. 3 is a view of the detail of the embedding of the electric wires.

WAYS OF CARRYING OUT THE INVENTION

With reference to the above figures, the ventilation tube particularly for medical devices, according to the invention, is generally designated by the reference numeral 1 and comprises a tubular body 2 made of flexible plastics, such as PVC, which is externally provided with ridges formed by a spiral ridge 3 which is rigidly coupled to the outer surface of the tubular body 2 since it is formed in a single extrusion process and is made of a more rigid plastics which allows to constitute the conventional spiral of a tube.

The particularity of the invention is constituted by the fact that two mutually spaced electric wires 4 and 5 are embedded directly inside the spiral ridge 3 and constitute an electric resistor.

The two electric wires are not in mutual contact and in practice the material that forms the ridge constitutes the electrical insulation for the copper wires.

Advantageously, two electric wires are used so that by simply joining them at one end an electric resistor is obtained with the possibility of connecting the remaining two ends to the electric power source.

The tubular body is advantageously made of transparent plastics, so that the tube remains transparent, and the direct insertion of the copper wires in the spiral ridge allows to considerably contain the weight of the tube as well as its manufacturing cost.

Another advantage obtained is constituted by the fact that the uniform distribution of the wires that form the electric resistor along the surface allows uniform heating in all points of the electrical surface while having excellent electrical safety characteristics, since the electric wires are directly embedded in the ridge, which is monolithic with the tube.

In practice, the materials employed, so long as they are compatible with the specific use, as well as the contingent shapes and dimensions, may be any according to requirements.

What is claimed is:
1. A ventilation tube for use with medical devices comprising:
  an elongate flexible, seamless, extruded plastic conduit having a uniform inside diameter;
  a helical plastic ridge formed on an outside diameter of said conduit;
  at least one wire conductor inserted directly in said ridge while said ridge is being extruded to form an electric resistor for heating a gas that flows inside the tube.

2. The ventilation tube of claim 1 wherein said ridge is formed from a plastic compound that is more rigid than a plastic compound of said conduit.

3. The apparatus of claim 1 wherein said elongate conduit has a proximal and distal end and said conductor is formed as a loop with two free ends, the free ends located al the proximal end of said conduit to connect to an electric power source.

4. The apparatus of claim 1, wherein said elongate conduit is formed from a transparent plastic compound.

5. The ventilation tube of claim 1 wherein the wires are uniformly embedded within the ridge to provide uniform heating in all points of the electrical surface.

6. The ventilation tube of claim 5 wherein the wires are made of copper.

7. The ventilation tube of claim 5 wherein the tube is made of a PVC material that is transparent.

8. The ventilation tube of claim 6 wherein the tube is made of a PVC material that is transparent.

9. A ventilation tube for use with medical devices comprising:
   an elongate flexible, seamless, extruded plastic conduit having a uniform inside diameter;
   a helical plastic ridge formed on an outside diameter of said conduit, said conduit and ridge being formed in a single extrusion process, said ridge being composed of transparent PVC;
   two copper wire conductors uniformly inserted directly in said ridge while said ridge is being extruded to form an electric resistor for heating a gas that flows inside the tube.

10. A process for making a ventilation tube for use with medical devices comprising:
    simultaneously extruding an elongate flexible, seamless, extruded plastic conduit having a uniform inside diameter and a helical plastic ridge formed on an outside diameter of said conduit;
    inserting wire conductors uniformly in said ridge while said ridge is being extruded to form an electric resistor for heating a gas that flows inside the tube.

11. The process claim 10 wherein the wires are uniformly embedded within the ridge to provide uniform heating in all points of the electrical surface.

12. The process of claim 11 wherein the wires are made of copper.

13. The process of claim 10 wherein the tube is made of a PVC material that is transparent.

* * * * *